(12) United States Patent
Gerber et al.

(10) Patent No.: US 8,529,525 B2
(45) Date of Patent: Sep. 10, 2013

(54) IMPLANTABLE VASCULAR ACCESS SYSTEM

(75) Inventors: Martin T. Gerber, Maple Grove, MN (US); Eric J. Fogt, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/357,594

(22) Filed: Jan. 24, 2012

(65) Prior Publication Data

US 2012/0245536 A1    Sep. 27, 2012

Related U.S. Application Data

(60) Provisional application No. 61/466,444, filed on Mar. 22, 2011.

(51) Int. Cl.
*A61M 37/00*    (2006.01)

(52) U.S. Cl.
USPC .................................. 604/288.01; 604/288.04

(58) Field of Classification Search
USPC ............................... 604/6.06, 288.01–288.04
See application file for complete search history.

(56) References Cited

U.S. PATENT DOCUMENTS

| | | | |
|---|---|---|---|
| 4,496,350 A * | 1/1985 | Cosentino | 604/175 |
| 4,892,518 A | 1/1990 | Cupp et al. | |
| 5,911,706 A | 6/1999 | Estabrook et al. | |
| 7,828,781 B2 * | 11/2010 | Edoga et al. | 604/288.02 |

* cited by examiner

*Primary Examiner* — Nicholas Lucchesi
*Assistant Examiner* — Leah Stohr
(74) *Attorney, Agent, or Firm* — Hahn & Voight PLLC; Kenneth J. Collier; Roger C. Hahn

(57) ABSTRACT

The invention relates to implantable vascular access ports that can release agents such as antibiotics, anti-thrombogenics and anti-proliferatives. The invention also relates to ports having locking mechanisms that prevent accidental disengagement, and structures that facilitate surgical implantation and provide for long-term stability and use of the port.

14 Claims, 16 Drawing Sheets

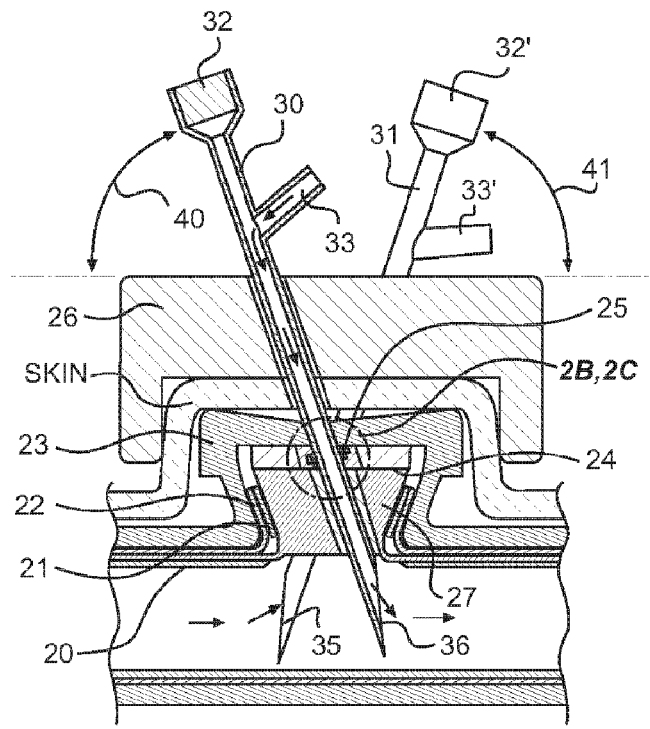
Figure 2A
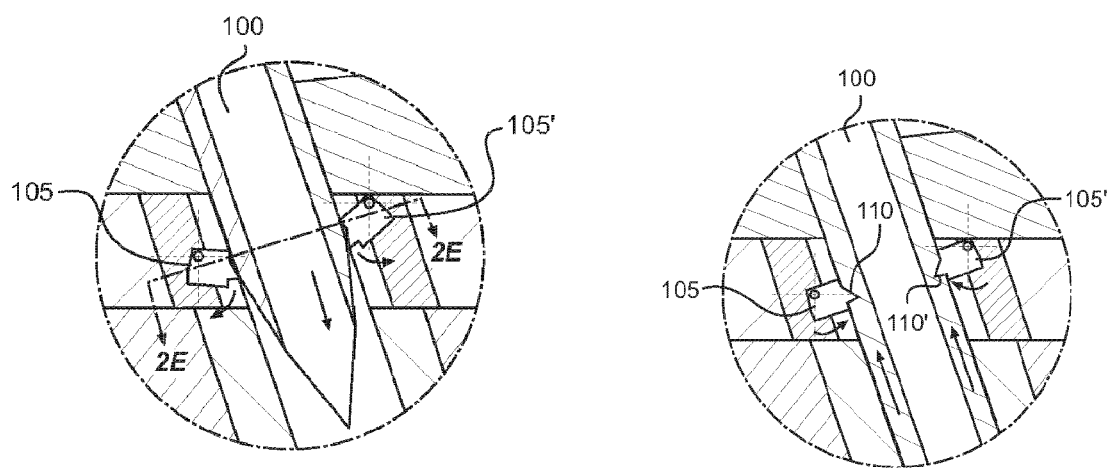
Figure 2B
Figure 2C

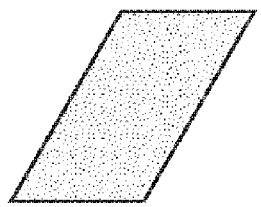
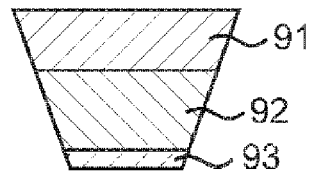
Figure 9G
Figure 9H
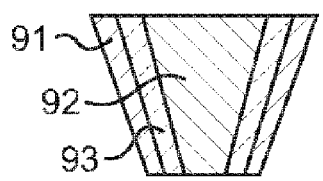
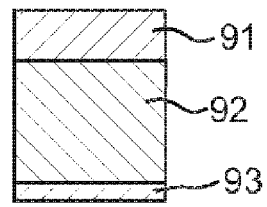
Figure 9I
Figure 9J
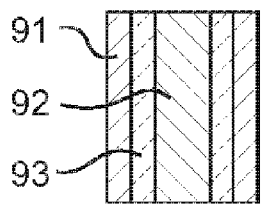
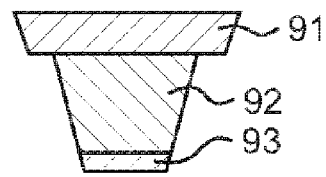
Figure 9K
Figure 9L

IMPLANTABLE VASCULAR ACCESS SYSTEM

CROSS-REFERENCE TO RELATED APPLICATIONS

This application claims benefit of priority to U.S. Provisional Patent Application Ser. No. 61/466,444, filed Mar. 22, 2011, which is incorporated herein by reference.

FIELD OF THE INVENTION

The invention relates generally to vascular access ports including implantable ports being configured to facilitate blood flow, and/or implantable ports having materials that release agents such as antibiotics, anti-thrombogenics and anti-proliferatives. The invention also broadly relates to vascular access ports having any one of locking mechanisms, structures which facilitate implantation structures which facilitate long-term stability, and combinations thereof.

BACKGROUND

Long-term blood access required for applications requiring repeated vascular access such as hemodialysis, ultrafiltration, and drug delivery, e.g. chemotherapy, can be problematic due to infection, stenosis, vessel patency, thrombogenesis, and patient compliance. Complications associated with vascular access procedures account for over 20% of hospitalizations of dialysis patients in the United States and cost about $1 billion annually. Although arteriovenous (AV) fistulas have been used for many years in dialysis and other forms of treatment, this procedure can have unfavorable outcomes, particularly in older patients, females, diabetics, and those having co-morbidities such as atherosclerotic vascular disease. Moreover, a maturation period is required subsequent to fistula surgery that may not be feasible in cases of rapid onset of disease. These considerations have led to increased utilization of AV grafts and decreased use of AV fistulas. However, AV grafts are prone to thrombosis usually arising from progressive stenosis at the draining vein, and increased incidence of infection. With regard to dialysis, the Dialysis Outcome Quality Initiative (DOQI) vascular access guidelines published by the National Kidney Foundation advocated the increased prevalence of fistula use among dialysis patients. These guidelines recommend attempting fistula placement in at least 50% of patients, with AV grafts being reserved for patients whose vascular anatomy does not permit construction of a native AV fistula. DOQI guidelines predict that such a strategy will result in 40% of prevalent patients dialyzing with a fistula.

However, deliberately placing AV fistulas in the majority of patients undergoing dialysis or other treatments requiring vascular access increases the frequency of failure due to the marginal nature of vessels within such patients. Moreover, treatment is generally inefficient using AV fistulas and grafts because the blood is withdrawn from and returned to the body using a single AV fistula or graft, particularly where a dual lumen needle is used instead of two needles, which are separated in placement in the fistula. Where there is dual use of the same access site, it is likely that treated and untreated blood will commingle resulting in recirculation or admixture of both treated and untreated blood. In addition, frequent use of needles in either a two-needle or single-needle dual lumen configuration can cause damage to the walls of the vessel rendering the access site unsuitable for treatment.

Implantable vascular access ports can be used to directly contact a vessel and typically consist of an arterial port and a venous port. The ports can improve the efficiency of hemodialysis by reducing admixture and recirculation by being placed on separate vessels. Damage to the wall of the vessels is also reduced because the needles are inserted only into the artificial port, rather than into the vessels themselves. For example, the arterial port can contact an artery using an arterial graft, and the venous port can contact a vein using a venous graft wherein a needle may be inserted into the arterial port for blood "draw" and another needle may be inserted into the venous port for blood "return" to connect the implantable device to the dialysis machine. Alternatively, an AV fistula is created where the blood "draw" is placed on the arterial side of the fistula and the "return" is placed on the venous side of the fistula. Oftentimes, access ports must be placed in close proximity to each other and can result in admixture and recirculation if the same vessel is used. In some cases, an anti-compression structure is used to prevent squeezing of the vessel during insertion of the needle but can be difficult to surgically implant due to the need for special screws and separate parts that must be joined. Specially adapted needles may be used to allow a healthcare practitioner to insert the needle to an appropriate and safe depth every time but operator error is still a problem resulting in suboptimal fluid flow and additional vessel trauma. Additionally, the design of the ports and needles precludes operation by a patient in the absence of technician supervision. Moreover, known access ports tend to slide or rotate on the vessel causing failure of the device particularly during insertion of the needle. During operation, the needle may be unintentionally dislodged by the operator. Although specially adapted needles may be used to allow an operator to insert the needle to an appropriate and safe depth, known access ports lack an optimal means for inserting the needle into the port at a pre-determined length and position. Further, known vascular access devices are not conducive to operation by the patient in which they are implanted due to the complexity of insertion instruments associated with known ports. Known vascular access devices also cause complications such as bleeding and infection, and can result in blood clotting and biocompatibility problems. Notably, interactions between blood components and the materials found within blood processing systems induce the activation of several biological systems such as platelets, complement, and coagulation cascades. Thrombin, an enzyme generated during coagulation, causes blood clotting within blood processing systems, reducing system efficiency. Conventional blood processing systems typically employ the use of anticoagulant drugs, such as heparin, to prevent the formation of blood clots. But prolonged use of anticoagulant drugs without control presents a significant risk of uncontrolled bleeding in patients. Further, known ports do not provide for simplified use or operation such that a patient can administer therapy at home that avoids separate injections of heparin or oversight by a skilled technician or hospital staff for safe and proper usage of the port.

Hence, there is a need for a new improved implantable access port that is an alternative to known vascular access devices and procedures used in ultrafiltration, drug delivery, and kidney dialysis procedures. There is a need for ports having increased patient comfort that reduces the risk of damage to the vessel and frequency of complications. The ports should be easy to use and improve the facility of conducting treatment by medical personnel. There is a need for a simple port that can be easily implanted. The ports should also be easily operated by either a technician or the patient in both clinical and home-use environments. The port must minimize admixture and recirculation. In addition, the port should be able to inhibit infection and thrombogenesis. Further, there is a need for a port that can be reliably affixed onto the vessel subsequent to implantation. The port should prevent squeezing of the vessel during insertion of a needle, cannula or trocar and should be specially configured so that an operator can insert the needle to an appropriate and safe depth every time. There is a need for the safe interchange of untreated and treated blood of a patient through an implanted vascular access port for dialysis or ultrafiltration that will result in increased patient comfort, ease of use by an operator, and will be suitable for longer use than known devices and techniques.

SUMMARY OF THE INVENTION

The invention is directed to a vascular access port that has a plug casing having one or more plugs that is adapted to receive a first and/or second cannula, trocar or needle to permit fluid communication from a vessel wherein the first cannula is positioned upstream in the same vessel relative to the second cannula. In another embodiment, the vascular access port has a plug casing having one or more plugs adapted to receive one or more cannulas to permit fluid communication from a distal side of the plug casing to a proximal side of the plug casing and a port frame concentric to the vessel wherein the port frame is adapted to retain the plug casing and prevent compression of the vessel during insertion of the cannulas, and a means for affixing the plug casing to the port frame. A port frame concentric to the vessel is also a part of the vascular port wherein the port frame is adapted to retain the plug casing and prevent compression of the vessel during insertion of the cannulas. A means for affixing the plug casing to the port frame is also contemplated. In one embodiment, the vascular access port has a first plug being positioned so that the first cannula is angled in a direction to facilitate flow into the first cannula, and a second plug is positioned so that the second cannula is angled in a direction to facilitate flow out of the second cannula. In another embodiment, the vascular access port has a separate guide that can be positioned over the implanted port wherein the guide can assist an operator to position the needle, trocar or cannula at a specified angle and direction relative to the vessel for insertion into the port. The port frame can be pared on one side to make a unique fitting such that the guide can only be positioned in one direction thereby avoiding operator error. The port frame can also be shaped in various geometric shapes to be keyed to a similarly shaped guide. The guide can have a guide hole that only permits a particular needle cross-section.

The invention also contemplates a vascular access port with a plug casing having a distal end to contact a vessel and a proximal end to contact subcutaneous tissue and one or more plugs disposed inside the plug casing. A port frame is concentric to the vessel that is intended to be accessed wherein the port frame is adapted to retain the plug casing and prevent compression of the vessel. The port also contains a means for affixing the plug casing to the port frame and a releasable locking system located in the proximal end of the plug casing to prevent accidental removal of a cannula upon insertion into the one or more plugs. In one embodiment, the vascular access port is releasable by rotating the cannula, needle or trocar. In another embodiment, the cannula, needle or trocar has a circumferential groove disposed at a specified position to permit locking and accurate positioning of the cannula, needle or trocar within the port. A ball mechanism can also be used to lock and position the cannula, needle or trocar within the port.

The invention is further directed to a vascular access port with a plug casing having a distal end to contact a vessel and a proximal end to contact subcutaneous tissue and one or more plugs disposed therein, wherein the plugs are composed of a self-sealing layer and layers of one or more materials that are capable of releasing agents into and onto the vessel or other tissue contacted by the port. The layers containing agents can be configured in planar or concentric form and can be impregnated with any one of antibiotics, anti-thrombogenics, anti-proliferatives and combinations thereof. A port frame concentric to the vessel is positioned over the plug casing wherein the port frame is adapted to retain the plug casing and prevent compression of the vessel. A means for affixing the plug casing to the port frame is contemplated. In one embodiment, the vascular access port has a skirt or patch that is connected to the plug casing or plug frame that flares from the distal end of the plug casing to contact the vessel.

Another invention is for a vascular access port with a plug casing having a distal end to contact a vessel and a proximal end to contact subcutaneous tissue and one or more plugs inside the plug casing with a mesh sleeve that can encase the vessel wherein the mesh sleeve is affixed to the plug casing. A port frame concentric to the vessel can be adapted to retain the plug casing and prevent compression of the vessel. A means for affixing the plug casing to the port frame is also contemplated.

One invention is for a vascular access port with a plug casing having a first end contacting a vessel and a second end extending in a perpendicular direction away from the vessel wherein one or more plugs located inside the port casing for insertion of a cannula, needle or trocar to permit fluid communication from the vessel through said plugs. A mesh sleeve can encase the vessel and has a mounting ring to secure the mesh sleeve to the plug casing. A retaining ring that locks onto the exterior of the mounting ring; and a hinged port frame having opposing cuffs that may be joined together and are shaped to encapsulate the plug casing, mounting ring, retaining ring, and at least a portion of the mesh sleeve. In one embodiment, the vascular access port has at one end of the cuffs at least one latch for securely assembling the hinged port frame.

Another invention is a vascular port having a guide that can be positioned over the vascular port, wherein the guide positions a first and second cannula at a specified angle and direction relative to a vessel.

Another invention is a vascular port having a guide that can be positioned over the vascular port wherein the guide is shaped to conform to a port frame when positioned over skin.

Another invention is a vascular port having a guide that can be positioned over the vascular port wherein a port frame is shaped to mate with the guide in only one direction.

Another invention is a vascular port having a guide that can be positioned over the vascular port having a needle shaped to match a guide hole in the guide.

Another invention is a vascular port having a guide that can be positioned over the vascular port wherein the guide releasably opens and closes.

Another invention is a vascular port having a cannula having a groove or indentation keyed to a specified length and a specified port frame shape, wherein the cross-section of the cannula can be keyed to a specified port frame shape.

Another invention is a vascular port having a plug casing affixed to a port frame by any one of interference fitting, screw and nut, and adhesion.

Another invention is a vascular port having a skirt that flares from a distal end of a plug casing to contact a vessel.

Another invention is a vascular port having plugs that are tapered.

Another invention is a vascular port having a plug that is substantially columnar and angled in opposing directions to facilitate flow into a first cannula and out of a second cannula.

Another invention is a vascular port having one or more plugs that are substantially conical and angled in opposing directions to facilitate flow into a first cannula and out of a second cannula.

Another invention is a vascular port having a mesh sleeve affixed to a plug casing by a retaining ring that locks onto an interior of the plug casing.

Another invention is a vascular port having a hinged port frame with opposing cuffs joined together and shaped to encapsulate a plug casing, a mounting ring, a retaining ring and at least a portion of a mesh sleeve, wherein one end of the cuffs have at least on latch for securely assembling the hinged port frame.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

BRIEF DESCRIPTION OF THE DRAWINGS

FIG. 2A is a cut-away side view of an implantable vascular access port implanted on a blood vessel.

FIG. 2B is a detailed side view of a cannula locking mechanism on the implantable vascular access port of FIG. 2A.

FIG. 2C is another detailed side view of a cannula locking mechanism on the implantable vascular access port of FIG. 2A.

FIGS. 9E-G show a side view of yet another embodiment of an implantable vascular access port plug constructed of one material.

FIGS. 9H-O show a side view of yet another embodiment of an implantable vascular access port plug constructed of three materials.

DETAILED DESCRIPTION OF THE INVENTION

Figure 1A:
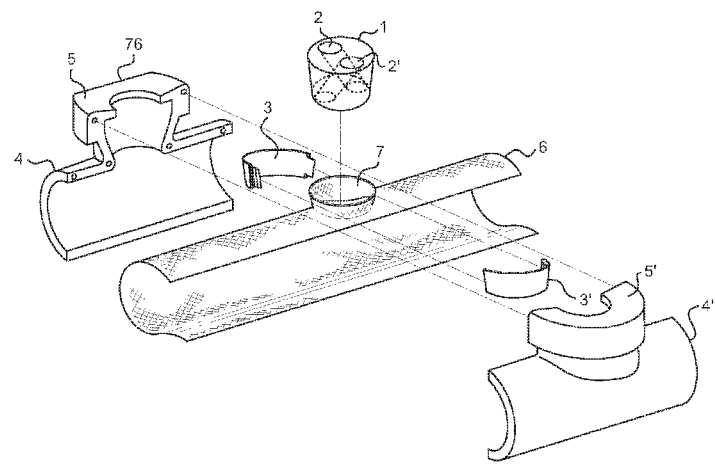
FIGS. 1A-D are exploded views of an implantable vascular access port.
Figure 1B:
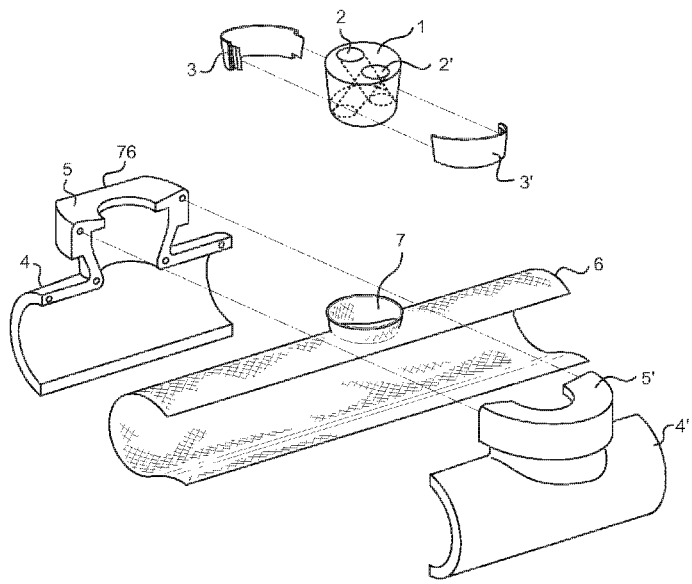
Figure 1C:
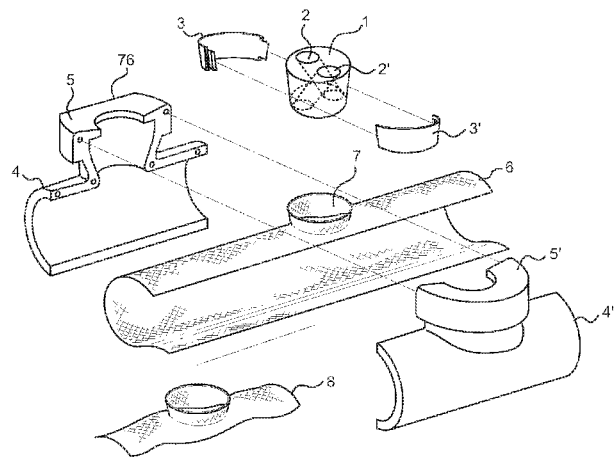

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. By way of example, "an element" means one element or more than one element.

The terms "administering," "administer," "delivering," "deliver," "introducing," and "introduce" can be used interchangeably to indicate the introduction of a therapeutic or diagnostic agent into the body of a patient in need thereof to treat a disease or condition, and can further mean the introduction of any agent into the body for any purpose.

A "biocompatible material" is a material that has the ability to interface with living biological tissues with an appropriate host response in any of specific medical systems, methods of treatment or delivery contemplated herein. The biocompatible material can consist of synthetic, natural or modified natural polymers intended to contact or interact with the biological systems during application of any of the inventions contained herein.

A "cannula," as used herein, is any tube used for the delivery or removal of fluid. In general, a cannula defines a passageway between two points. The cross-section of the cannula can be circular, rectangular, oval, hexagonal, octagonal, or any other geometric shape. The cannula may have a proximal end, a distal end and a bore therethrough. The bore of the cannula may be sized and configured to receive a trocar to assist during the insertion of the cannula into a material desired to be penetrated such as a patient's blood vessel. The cannula can be flexible, semi-rigid, or rigid. A rigid cannula may have a sharp tip capable of penetrating a desired material such as a self-sealing membrane, polymer, silicone rubber or a patient's skin, and combinations thereof. For such sharpened and rigid cannula, a trocar may not be required to penetrate a target material. A cannula may also have an angled tip suitable for receiving or discharging fluid. For a flexible or semi-rigid cannula, the interior of the cannula may be stiffened by a rod or trocar during insertion.

The term "upstream" means a point higher in the direction of flow relative to one point. The term "downstream" means a point lower in the direction of flow relative to one point.

"Chronic kidney disease" (CKD) is a condition characterized by the slow loss of kidney function over time. The most common causes of CKD are high blood pressure, diabetes, heart disease, and diseases that cause inflammation in the kidneys. Chronic kidney disease can also be caused by infections or urinary blockages. If CKD progresses, it can lead to end-stage renal disease (ESRD), which occurs when the glomerular filtration rate (GFR) is lower than 15 ml/min.

The terms "communicate" and "communication" include, but are not limited to, the connection of system fluid elements enabling fluid interface among and between said elements.

As used herein, the term "compression" refers to a force that tends to shorten or squeeze something, decreasing its volume.

The term "comprising" includes, but is not limited to, whatever follows the word "comprising." Thus, use of the term indicates that the listed elements are required or mandatory but that other elements are optional and may or may not be present.

The term "concentric" refers to the property of having a common center.

The term "consisting of" includes and is limited to whatever follows the phrase the phrase "consisting of." Thus, the phrase indicates that the limited elements are required or mandatory and that no other elements may be present.

As used herein, the term "cuff" refers to a closeable, substantially cylindrical band.

A "distal" end of an object is the end that is situated farthest from a point of attachment or origin, and the end closest to the point of attachment or origin is known as the "proximal" end.

"Dialysis" is a type of filtration, or a process of selective diffusion through a membrane. Dialysis removes solutes of a specific range of molecular weights via diffusion through a membrane from a fluid to be dialyzed into a dialysate. During dialysis, a fluid to be dialyzed is passed over a filter membrane, while dialysate is passed over the other side of that membrane. Dissolved solutes are transported across the filter membrane by diffusion between the fluids. The dialysate is used to remove solutes from the fluid to be dialyzed.

"Hemodialysis" is a technique where blood and a "cleansing fluid" called dialysate are exposed to each other separated by a semipermeable membrane. Solutes within the permeability range of the membrane pass while diffusing along existing concentration gradients. The sieving properties of the membrane exclude all solutes above a certain threshold from crossing the membrane. One common sieving property is "albumin sieving." Albumin is used to measure lymphatic absorption wherein the term "albumin sieve coefficient" can be used to describe a membrane property.

The term "mesh" means an openwork fabric or structure, such as an arrangement of interlocking metal links or wires with small openings between.

The term "needle" as used herein refers to a sharp pointed medical implement having one or two hollow lumens therein. In the case of two hollow lumens, the needle may be alternatively described as a "dual lumen needle."

An "obturator" as used herein is a rod that may be inserted into a trocar cannula. An obturator has a sharp point capable of piercing a patient's skin.

A "patient" or "subject" is a member of any animal species, preferably a mammalian species, optionally a human. The subject can be an apparently healthy individual, an individual suffering from a disease, or an individual being treated for a disease.

As used herein, the phrase "planar configuration" refers to an arrangement within the same two-dimensional plane.

The terms "pressure differential" and "pressure drop" refer to the difference in pressure measurements of a fluid between two points of measurement.

The term "rigid" means incapable of or resistant to bending.

The term "sleeve" refers to a small case or tube into which an object fits.

The term "stylet" is a type of obturator and as used herein refers to a shaft with a sharp, needlelike tip that is insertable in a trocar cannula.

The terms "treating" and "treatment" refer to the management and care of a patient having a pathology or condition for which administration of one or more therapeutic compounds is indicated for the purpose of combating or alleviating symptoms and complications of the condition. Treating includes administering one or more formulations of the present invention to prevent or alleviate the symptoms or complications or to eliminate the disease, condition, or disorder. As used herein, "treatment" or "therapy" refers to both therapeutic treatment and prophylactic or preventative measures. "Treating" or "treatment" does not require complete alleviation of signs or symptoms, does not require a cure, and includes protocols having only a marginal or incomplete effect on a patient.

A "trocar," as used herein is a sharply pointed shaft designed to penetrate a material such as a skin, blood vessel, polymer or rubber, and combinations thereof. In certain embodiments, the trocar can be removably inserted into a "trocar cannula."

A "trocar cannula," as used herein is an instrument for introducing a cannula into a patient's blood vessel. A trocar cannula may be introduced into a patient by a removable obturator having a sharp point capable of piercing a patient's skin. In certain configurations, the trocar passes through materials such as self-sealing septum made from silicone rubber without damaging the septum material to define a fluid passageway between two points.

As used herein, the phrase "vascular access" refers to the ability to enter a blood vessel.

The term "implantable," as used herein describes a device, component or module intended to be totally or partially introduced, surgically or medically into a mammalian body, or by medical intervention that remains after the procedure.

The term "biocompatible material," as used herein describes a material that can perform with an appropriate response for the specific application of an implantable access port. The term does not exclude any response and can include aggressive or cytotoxic responses.

The present invention provides long-term access to a patient's vasculature with reduced vascular deterioration and risks of infection. The invention is suitable for providing repetitive access to a patient's vasculature for intravenous drug delivery and the treatment of chronic kidney disease via hemodialysis.

The present invention consists essentially of one or more implantable vascular access ports connected to a patient's vasculature, an access alignment device, and an insertion device.

Simplified representations of embodiments of implantable vascular access ports according to the present invention are shown in FIGS. 1A-1D. In general, an access port includes a plug casing with plugs, a support mesh, and an anti-compression frame that is also described herein as a port frame. As shown in FIGS. 1A-1D, a plug casing 1 includes embedded plugs 2. The plug casing 1 is located above an incision on a patient's blood vessel. A support mesh 6 encases the patient's blood vessel, and includes a mounting ring 7 located around the blood vessel incision. The mounting ring 7 receives the plug casing 1 in position over the blood vessel incision. In some embodiments, a retaining ring 3 secures the mesh mounting ring 7 to the plug casing 1. The retaining ring 3 is made up of two separate halves which snap together around the mesh mounting ring 7 and plug casing 1 to secure the mesh mounting ring and plug casing 1 together. In other embodiments, the retaining ring 3 acts as a spacer between the plug casing 1 and the mounting ring 7. A port frame 4 includes a collar 5, and encases the support mesh 6, mounting ring 7, retaining ring 3 and plug casing 1 over the patient's blood vessel.

Figure 1D:
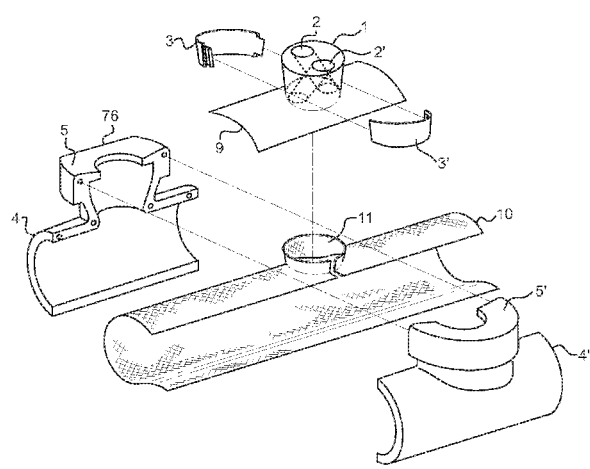

As shown in FIG. 1D, the plug casing 1 may include a skirt 9 that flares from the end of the plug casing 1 near the blood vessel for added stability of the port structure. The skirt 9 may be attached to the blood vessel via a suitable biocompatible material or structure such as fibrin glue, sutures, or surgical clamps.

The plug casing 1 is constructed of a biocompatible material such as polytetrafluoroethylene, polyethylene terephthalate ("PET"), polytetrafluoroethylene ("PTFE"), silicone, polyurethane, or a combination thereof. The skirt 9 may be made of the same material as the plug casing 1 and may be an extension thereof. Alternatively, the skirt 9 may be constructed of a porous fibrogenic mesh attached to the plug casing 1 via an ultrasonic weld or biocompatible adhesive. The mesh may be treated with a surface coating of fibrosis-inducing agents, or extracellular matrix components which promote the growth of fibrous tissue. The mesh may also be impregnated with a slow-release pharmacological agent which promotes fibrous tissue growth. The skirt 9 is preferably flexible in order to conform to the curvature of the blood vessel on which it is mounted.

The support mesh 6 facilitates the securing and attachment of the plug casing 1 to a patient's blood vessel. The support mesh 6 forms a sleeve around the blood vessel and includes a mounting ring 7 which surrounds the vessel incision and the portion of the plug casing 1 near the blood vessel. The mounting ring may be made of the same material as the support mesh and may be an extension thereof. The mounting ring may also be a molded rigid material that is attached to the support mesh. The structure of the mesh 6 may be formed of woven or braided fibers. The fibers may be made of a biocompatible material such as PET, PTFE, polypropylene, stainless steel, MP35 alloy, nitinol, tantalum, ceramic, nickel, titanium, aluminum, niobium, and high carat gold. Additionally, the materials of the mesh 6 may be porous, or treated with a surface coating of fibrosis-inducing agents, or extracellular matrix components which promote the growth of fibrous tissue. The materials of the mesh 6 may also be impregnated with a slow-release pharmacological agent which promotes fibrous tissue growth. In embodiments that include a support mesh 6 constructed of a fibrogenic material, fibrous tissue builds up over the fibrogenic mesh during a maturation period, and improves the anchoring of the mesh 6 to the surface of the blood vessel thereby enhancing long-term stability of the access port.

The support mesh 6 is configured to be wrapped around the outer surface of the blood vessel at the vessel access site. The mesh 6 may be sufficiently flexible to conform to the outer surface of the blood vessel. Referring to FIGS. 2A, 3, 4, and 5, in embodiments having a skirt, the support mesh 22 encases the skirt to protect the connection of the skirt to the blood vessel, to maintain vessel shape and structure, and to prevent the plug casing 27 from shifting position.

Multiple means for attaching the support mesh to a blood vessel are contemplated. As indicated in FIGS. 1A-1D, in some embodiments the support mesh 6 may be wrapped around the vessel, and overlapped back onto itself. Once wrapped in place, the mesh 6 may then be secured by suturing or clamping the overlapping segments together, affixing the overlapping segments together with adhesive, or affixing the mesh to the vessel with adhesive. Additional attachment means include any other biologically suitable materials or attachment structures.

Referring to FIGS. 1A-1D, the port frame 4 encases the support mesh 6 and plug casing 1 on the blood vessel as discussed. In some embodiments, when the port frame 4 is in place, the frame collar 5 encircles and compresses the retaining ring 3 around the mesh mounting ring 7 and the plug casing 1 creating a tight fit of said elements.

The port frame 4 is constructed of a rigid biocompatible material such as PET, PTFE, or titanium. The rigidity of the port frame 4 prevents deformation of the blood vessel when pressure is exerted against the plug casing 1 by insertion forces during port access. The port frame 4 evenly distributes the insertion forces across the rigid frame material thereby preventing deformation of the blood vessel.

Figure 7A:
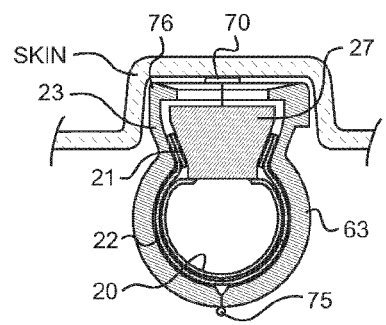
FIG. 7A is an end view of an implantable venous access port with a hinged anti-compression frame.
Figure 7B:
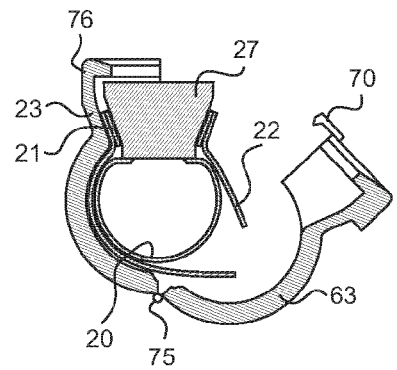
FIG. 7B is another end view showing the hinged port frame of FIG. 7A in an open position.
Figure 7C:
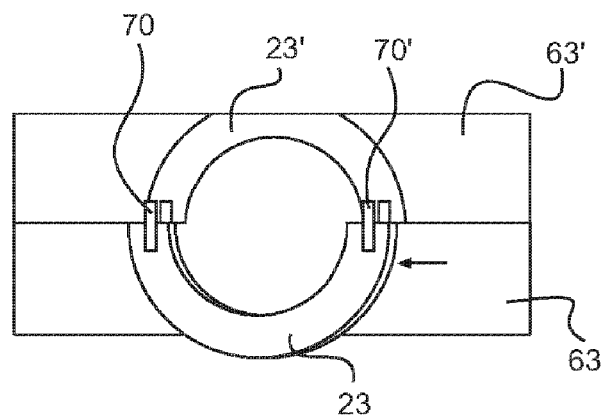
FIG. 7C is a top view showing a shearing force applied to the hinged port frame of FIGS. 7A and 7B.

Referring to FIGS. 7A-7C, the port frame 63 may include a hinge 75 which allows the port frame 63 to be opened and closed. The hinge 75 facilitates fitting the port frame 63 around a blood vessel and the plug casing 27 during implantation of the vascular access port by simplifying alignment of the port frame around the plug casing 27. In some embodiments a latch 70 allows the port frame 63 to be locked in a closed configuration. Once locked, the port frame 63 can be opened by applying a shearing force as shown in FIG. 7C. In other embodiments, two hinges can be disposed on an upper side wall (not shown) of the port frame wherein two sides of the port frame come together and latch together at a bottom of the port frame to surround the plug casing.

Figure 8A:
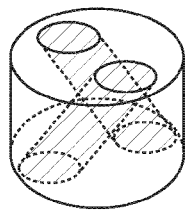
FIGS. 8A-E show a semi-transparent perspective view of an embodiment of a plug frame of an implantable vascular access port.
Figure 8B:
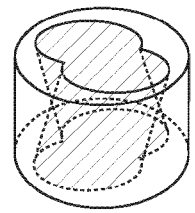
Figure 8C:
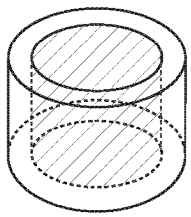
Figure 8D:
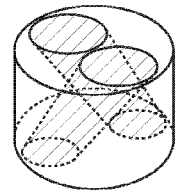
Figure 8E:
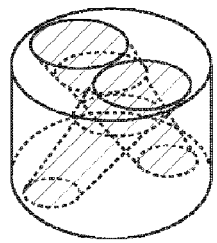
Figure 9A:
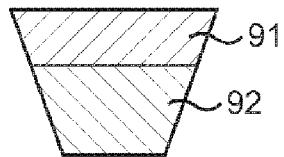
FIGS. 9A-D show a side view of an embodiment of an implantable vascular access port plug constructed of two materials.
Figure 9B:
Figure 9C:
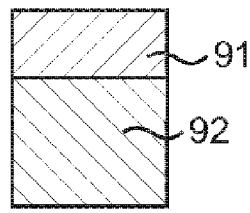
Figure 9D:
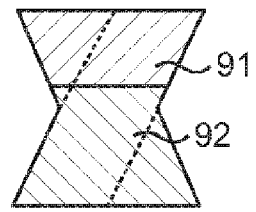
Figure 9E:
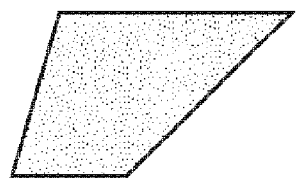
Figure 9F:
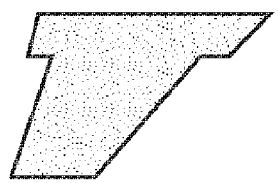
Figure 9M:
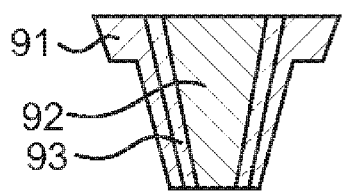
Figure 9N:
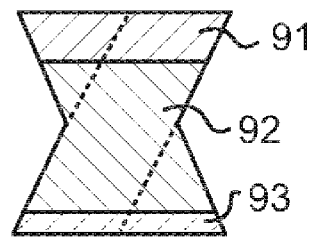
Figure 9O:
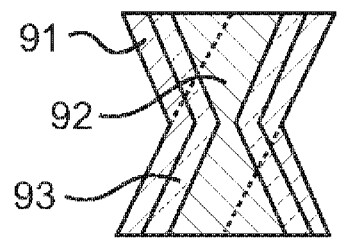

The plug casings of the present invention include one or more plugs which are now described in more detail. Some embodiments of a plug casing are configured to accommodate two insertion devices as shown in FIGS. 8A, 8B, 8D, and 8E. Referring specifically to FIGS. 8A, 8D, and 8E, two separate plugs are embedded within the plug casing wherein each plug receives a separate insertion device. As shown in FIGS. 8A, 8D, and 8E, the plugs may be cylindrical or conical. Referring specifically to FIG. 8B, a single plug is configured to receive two insertion devices. Another embodiment of a plug casing is configured to receive a single insertion device as shown in FIG. 8C. Several shapes of the plug are contemplated as shown in FIGS. 9A-9O.

In some plug casing embodiments, the plug includes a self-sealing membrane. Multiple configurations of the self-sealing membrane 91 within the plug are shown in FIGS. 9A-9D and 9H-9O. The self-sealing membrane 91 is constructed and arranged to allow an insertion device to be inserted into the blood vessel, and to reseal upon removal of the insertion device. The self-sealing membrane may be constructed of a silicone material. Self-sealing silicone membranes or septums are well known in vascular access systems to provide access for infusion of fluids and/or aspiration of blood.

In addition to include a self-sealing membrane, some embodiments of the plug may be constructed of a plurality of materials, wherein each material is configured to release a different agent. Such agents include antiproliferative agents, antithrombogenic agents, and antibiotic agents. Antiproliferative agents include any antiproliferative suitable for use in a human and include but are not limited to taxol, paclitaxel, rapamycin, tacrolimus, everolimus, actinomycin, methotrexate, angiopeptin, vincristine, mitocycin, statins, C-MYC antisense, sirolimus, restenASE, 2-chloro-deoxyadenosine, PCNA (proliferating cell nuclear antigen) ribozyme, batimastat, prolyl hydroxylase inhibitors, halofuginone, C-proteinase inhibitors, and probucol; and combinations and/or derivates thereof. Antithrombogenic agents include any antithrombogenic suitable for use in a human such as heparin. Antibiotic agents include any antibiotic suitable for use in a human and include but are not limited minocycline, rifampin, erythromycin, nafcillin, cefazolin, imipenem, aztreonam, gentamicin, sulfamethoxazole, vancomycin, ciprofloxacin, trimethoprim, metronidazole, clindamycin, teicoplanin, mupirocin, azithromycin, clarithromycin, ofloxacin, lomefloxacin, norfloxacin, nalidixicacid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole, and nystatin. One skilled in the art will recognize that different materials may be loaded with different agents to address specific needs. For example, plug material abutting the patient's skin may contain an antibacterial agent, and plug material abutting the blood vessel may contain an anti-inflammatory agent. In plug embodiments having a plurality of materials, said materials may be joined together via ultrasonic welding, biocompatible adhesive, or compression fittings.

FIGS. 9A-9D and 9H, 9J, 9L, and 9N show embodiments of plugs constructed of a plurality of stacked materials. Each embodiment includes a layer of self-sealing material 91 and one or more planar layers of different agent releasing materials 92 and 93 arranged underneath.

FIGS. 9I, 9K, 9M, and 9O show embodiments of plugs constructed of a plurality of concentric materials. Each embodiment includes one or more agent releasing layers 92 and 93 disposed concentrically around a core of self-sealing material 91.

Multiple port configurations are contemplated. One port configuration embodiment includes a dual channel port that accesses a blood vessel at a single location as shown in FIGS. 2A, 3, 4, and 5. In embodiments having dual channels, each port channel is angled and arranged at an opposing direction relative to the other in order to obtain optimum hemodynamics and blood flow profile.

Another port configuration embodiment includes two single channel ports which access the same type of blood vessel at different locations. Alternatively, one single channel port can access one type of blood vessel, and another single channel port can access a differing type of blood vessel. The channel on each port is angled to obtain an optimum blood flow profile into the channel.

Another port configuration embodiment includes one single channel port. A dual-lumen cannula or needle may be used in a single port to obtain two separate channels.

Access ports according to the present invention permit access to a blood vessel within a patient via an insertion device. Such devices facilitate the insertion of a cannula into a patient's blood vessel and include trocar cannulas. The introduction of a cannula into a patient via a trocar cannula is well known within the art. In general, a trocar cannula includes a cannula and an obturator with a sharp point. According to embodiments of the present invention, a trocar cannula is inserted through a patient's skin and into a plug of an access port to deliver a cannula into a blood vessel. Entry of the trocar cannula into a patient's blood vessel is enabled by the sharp point of the obturator. The sharp point on the obturator pierces a patient's skin and accesses the implanted port underneath. The sharp point of the obturator is designed to prevent damaging the plug septum during insertion. Once the trocar cannula is introduced into the port, the obturator is removed from the trocar cannula. In other embodiments, the cannula is rigid and sharpened thereby avoiding the need for a removable sharp point to penetrate the patient's skin and plug. For example, the sharp point is a non-coring needle such as a Huber needle, which has a ninety degree bend for use with a port, which does not employ an obturator. In other embodiments, a needle may be used to penetrate the skin and plug wherein the needle is in fluid communication with tubes to receive or deliver blood to a vessel.

Figure 2D:
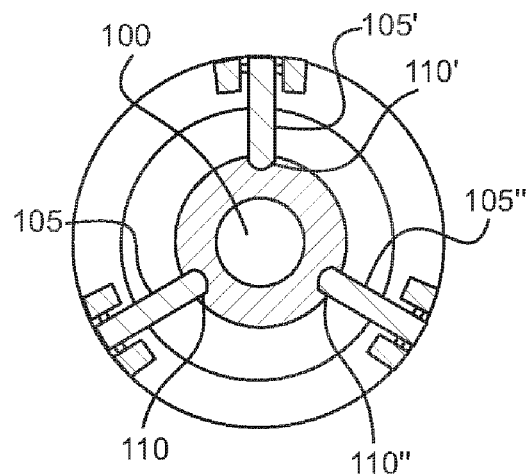
FIG. 2D is a detailed top view of the cannula locking mechanism of FIGS. 2B and 2C.
Figure 3:
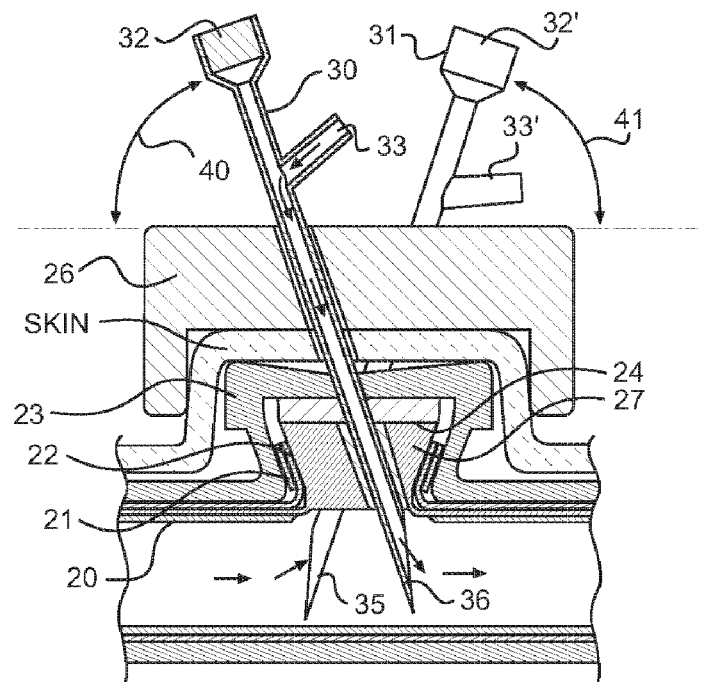
FIGS. 3-5 are a cut-away side view of another embodiment of an implantable vascular access port implanted on a blood vessel.
Figure 4:
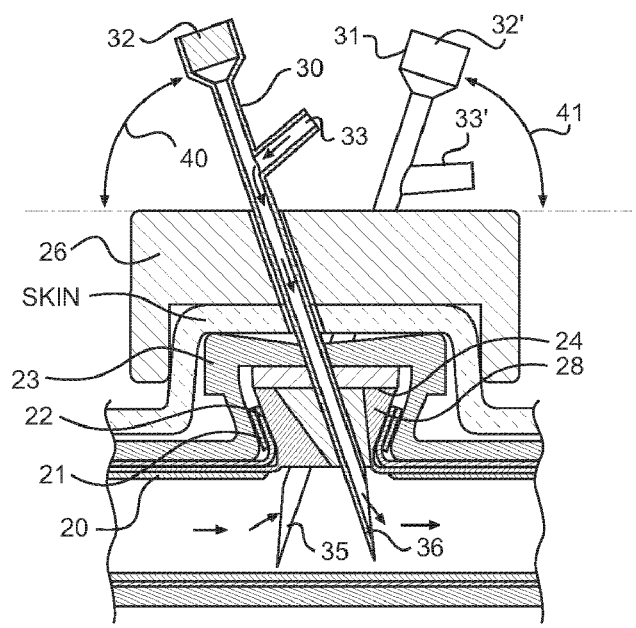

Referring to FIGS. 2A, 3, 4, the obturator is removed through a self-sealing obturator septum 32 which seals the obturator opening of the trocar cannula upon removal of the obturator. The self-sealing septum may be a silicone rubber membrane. Once the trocar cannula is inserted into the blood vessel, a cannula port 33 can be used to deliver or receive fluid to and from the blood vessel. Straight cannulas of the present invention may have angled tips 35 and 36 to facilitate receiving and discharging fluid therefrom.

Figure 5:
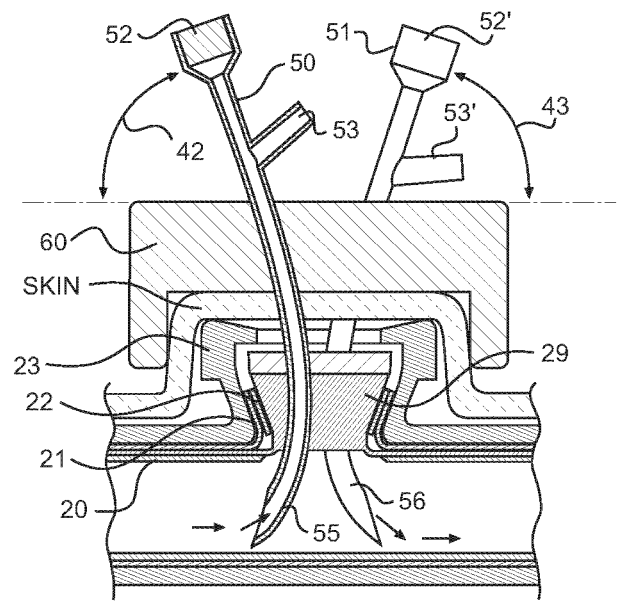

Referring to FIG. 5, the obturator in a curved trocar cannula is removed through a self-sealing obturator septum 52 which seals the obturator opening of the trocar cannula upon removal of the obturator. The obturator is angled such that removal from the trocar cannula is easily accomplished. The self-sealing septum may be a silicone membrane. Once the trocar cannula is inserted into the blood vessel, a cannula port 53 can be used to deliver or receive fluid to and from the blood vessel. Curved cannulas of the present invention may have angled tips 55 and 56 to facilitate receiving and discharging fluid therefrom.

Flow rates in and out of access ports according to the present invention are dependent on several factors including the angle of trocar cannula insertion within the blood vessel. Referring to FIGS. 2A, 3, and 4, the angles of insertion 40 and 41 of a straight trocar cannula are indicated. The angles can range from 5 to 90° and can be selected from any one of the non-limiting ranges from 5 to 25°, 5 to 30°, 30 to 45°, 30 to 60°, 30 to 90°, 60 to 90°, or 75 to 90°. Referring to FIG. 5, the angles of insertion 55 and 56 of a curved trocar cannula are indicated.

An insertion guide may be used to ensure a specific angle of trocar cannula insertion into the access port and blood vessel. As shown in FIGS. 2A, 3, 4, 6A and 6B, an embodiment of a guide 26 for a straight trocar cannula fits over the portion of a patient's skin residing above an access port, and mates with the port frame collar 23 to ensure proper alignment over the port plug. As shown in FIG. 5, another embodiment of a guide 60 for a curved trocar cannula fits over the portion of a patient's skin residing above an access port and mates with the port frame collar 23 to ensure proper alignment over the port plug.

In some embodiments, the guide includes angled insertion holes which have diameters slightly larger than the diameter of the trocar cannulas to be inserted therein. The matched diameters of the insertion holes and the trocar cannula restrict the lateral movement of the trocar cannula during insertion in order to ensure proper alignment.

Figure 6A:
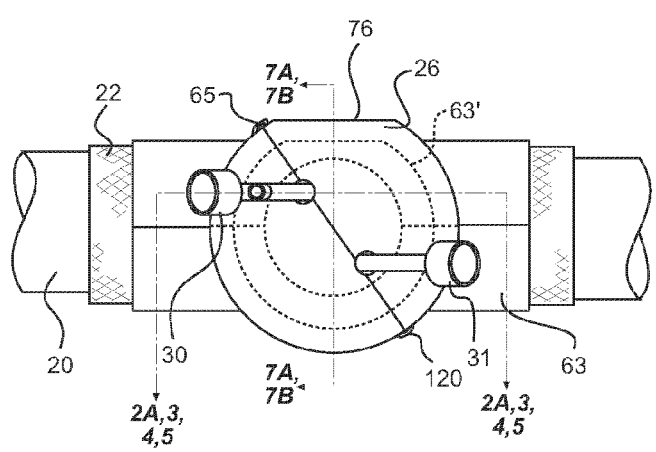
FIG. 6A is a top view of an alignment guide mounted on an implantable vascular access port.
Figure 6B:
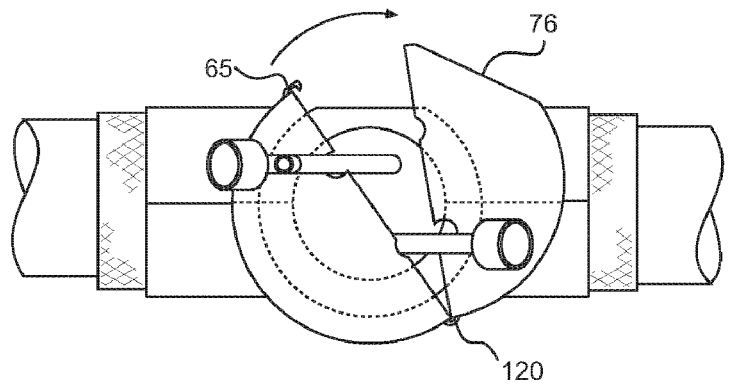
FIG. 6B is another top view of the alignment guide of FIG. 6A.

Referring to FIGS. 6A and 6B, the guide 26 may include a flat side 76 or be otherwise shaped to match a specific shape of the port frame collar to ensure proper alignment of the guide over the vascular access port. In some embodiments, the guide may include a hinge 120 as also shown in FIGS. 6A and 6B. The hinge 120 allows the guide to be opened in order to easily remove it once the trocar cannulas are in place. A latch 65 may be included on the guide to maintain the guide in a closed position during trocar insertion. The guide may also be maintained in a closed configuration by magnets, hooks, and the like.

The insertion guide may include spacers that serve as stops to control the depth at which the trocar cannulas are inserted. The dimensions of the spacers and the angles of the guide holes may be tailored to suit the differences in anatomies among patients, and may be color-coded for ease of identification. Additionally, the guide may include an audible click mechanism to indicate when an inserted trocar cannula has reached the correct depth within a patient.

Figure 2E:
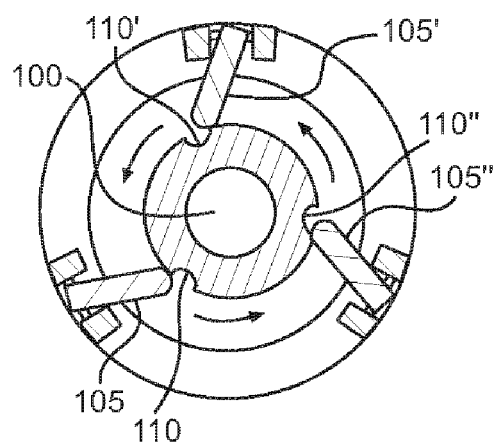
FIG. 2E is another detailed top view of the cannula locking mechanism of FIGS. 2B and 2C.

During blood vessel access, it is important that the trocar cannulas remain in place within the access port once the obturator is removed. Accordingly, access ports of the present invention may include a locking system to prevent unintended removal of an inserted trocar cannula. Referring to FIGS. 2A-2E, an embodiment of a locking system is described. A trocar cannula lock 25 is included above each port on the plug casing 27. The lock 25 includes pivoting locking teeth 105 and 105' which extend radially inward and interface with indentations 110 and 110' on an inserted trocar cannula 100 as shown in FIGS. 2B-2E. Specifically, the locking teeth 105 and 105' allow passage of a trocar cannula 100 by pivoting from a locked position in the direction of trocar cannula insertion as shown in FIGS. 2D and 2E. Once the lock indentations 110 and 110' of the trocar cannula 100 reach the locking teeth 105 and 105', the teeth pivot back to a locked position and interface with the lock indentations as shown in FIG. 2C to prevent removal of the trocar cannula. The locking teeth 105 and 105' also pivot in a direction perpendicular to the direction of trocar cannula insertion in order to enable intentional removal of the trocar cannula 100 as shown in FIGS. 2D and 2E. Intentional removal is accomplished by axially twisting the trocar cannula 100 to disengage the locking teeth 105 and 105' from the trocar cannula lock indentations 110 and 110'. Once the locking teeth 105 and 105' are disengaged, the trocar cannula 100 may be removed from the port.

In addition to locking the trocar cannula in place, the location of the cannula lock indentations can also fix the depth of trocar cannula insertion within a patient's blood vessel. One skilled in the art will recognize that trocar cannulas with varying locations of lock indentations can be used to achieve different insertion depths in order to accommodate different patient anatomies and access port locations.

Figure 10A:
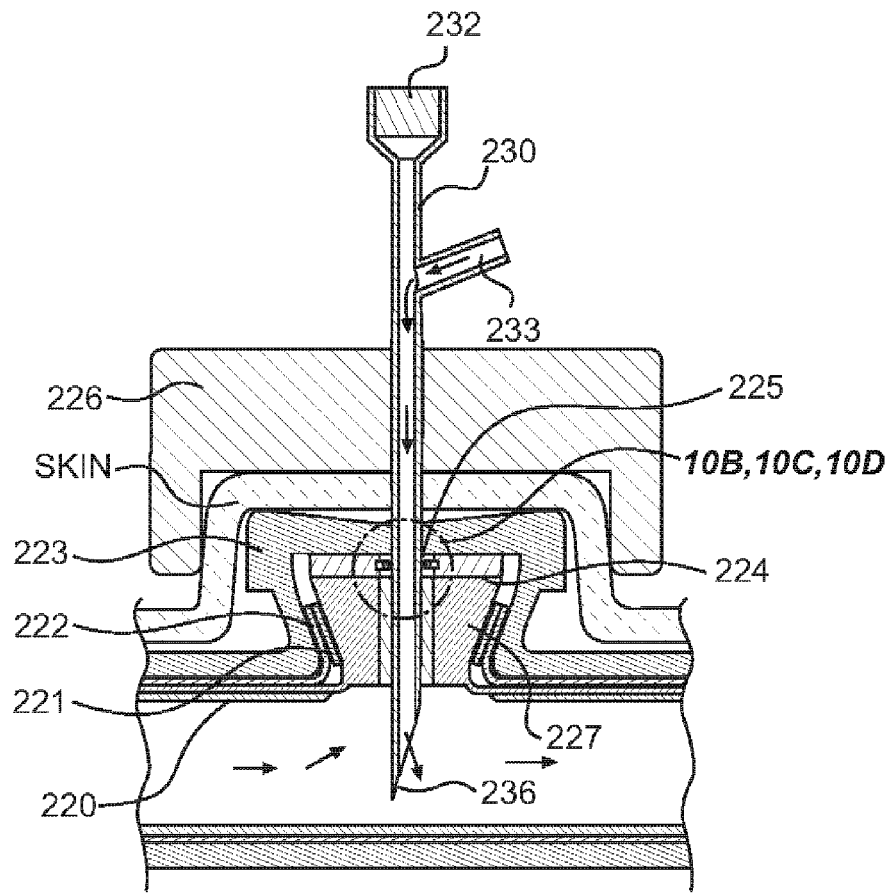
FIG. 10A is a cut-away side view of a single channel implantable vascular access port implanted on a blood vessel.
Figure 10B:
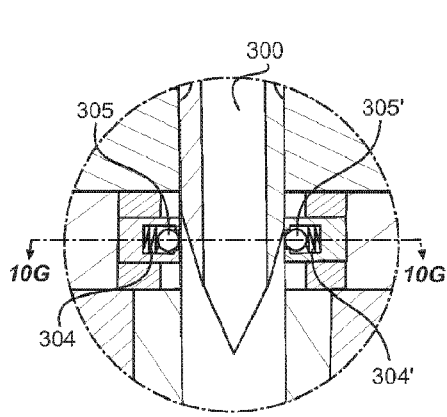
FIG. 10B is a detailed side view of a cannula ball locking mechanism on the implantable vascular access port of FIG. 10A.
Figure 10C:
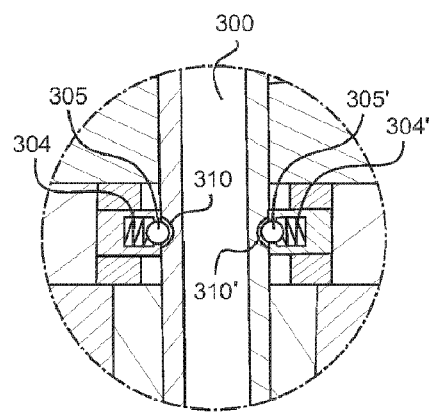
FIG. 10C is another detailed side view of a cannula ball locking mechanism on the implantable vascular access port of FIG. 10A.
Figure 10D:
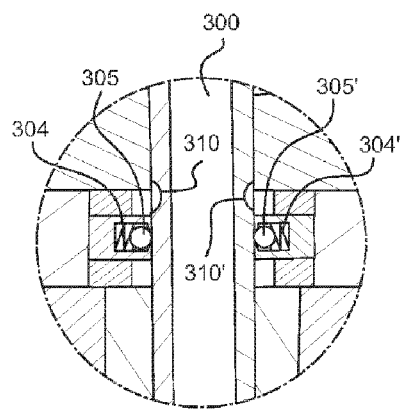
FIG. 10D is another detailed side view of a cannula ball locking mechanism on the implantable vascular access port of FIG. 10A.
Figure 10E:
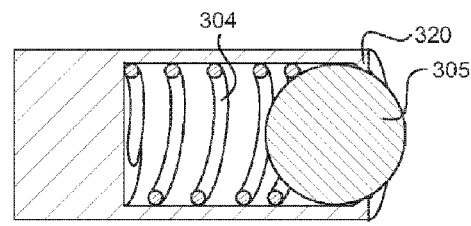
FIG. 10E is a detailed cut-away side view of a ball bearing spring lock on the ball locking mechanism of FIGS. 10B-D.

Referring to FIGS. 10A-10E, another embodiment of a locking system is described. A trocar cannula lock 225 is included above the port on the plug casing 224. The lock 225 includes spring-mounted ball bearings 305 and 305' arranged radially around the inner surface of the lock. Springs 304 and 304' push the ball bearings 305 and 305' inward toward the center of the lock in the absence of a trocar cannula 300. When a trocar cannula 300 is inserted into the lock, the ball bearings 305 and 305' are pressed outward radially into the walls of the lock by the walls of the trocar cannula as shown in FIGS. 10B and 10D. Once ball lock indentations 310 and 310' of the trocar cannula 300 reach the ball bearings 305 and 305', the bearings spring back to a locked position and interface with the ball lock indentations as shown in FIG. 10C to prevent removal of the trocar cannula. In other embodiments, the indentations can be configured as a single circumferential groove disposed on the outside surface of cannula (not shown) to engage the ball lock mechanism at a specified length.

Figure 10F:
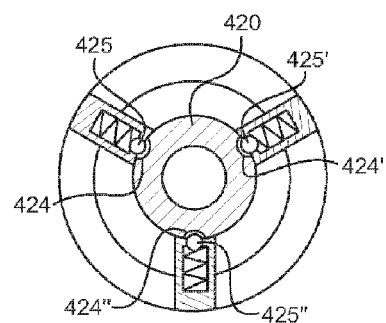
FIG. 10F is a detailed top view of a circular cannula ball locking mechanism.
Figure 10G:
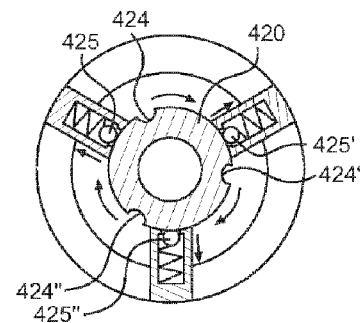
FIG. 10G is another detailed top view of a circular cannula ball locking mechanism.

One embodiment of a ball lock system with a trocar cannula having a circular cross section is shown in FIGS. 10F and 10G. The ball bearings 425, 425', and 425" interface with ball lock indentations 424, 424', and 424" on a circular trocar cannula 420 to inhibit unintended axial movement of the trocar cannula in a locked position, but permit rotational movement of the trocar cannula to disengage the interface of the ball bearings from the ball lock indentations on the trocar cannula as shown in FIGS. 10F and 10G. Alternatively, the interface of the ball bearings 425, 425', and 425" from the ball lock indentations 424, 424', and 424" on the trocar cannula 420 may be disengaged by applying sufficient axial force. Once the ball bearings 425, 425', and 425" are disengaged, the trocar cannula 420 may be removed from the port. In other embodiments, the indentations can be configured as a single circumferential groove disposed on the outside surface of cannula (not shown) to engage the ball lock mechanism at a specified length.

Figure 10H:
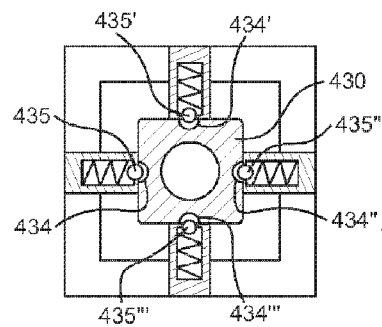
FIG. 10H is a detailed top view of a rectilinear cannula ball locking mechanism.
Figure 10I:
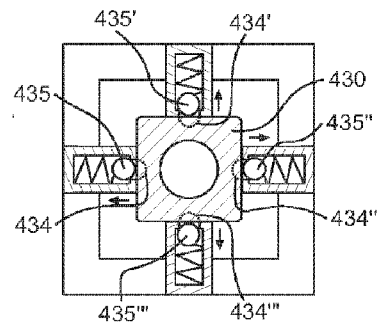
FIG. 10I is another detailed top view of a rectilinear cannula ball locking mechanism.

Another embodiment of a ball lock system with a trocar cannula having a rectilinear cross section is shown in FIGS. 10H and 10I. The ball bearings 435, 435', 435", 435''' can interface with ball lock indentations 434, 434', 434" and 434''' on a rectilinear trocar cannula 430 to inhibit unintended axial movement of the trocar cannula in a locked position. Sufficient axial force applied to the trocar cannula 430 disengages the interface of the ball bearings 435, 435', 435" and 435''' from the ball lock indentations 434, 434', 434" and 434''' on the trocar cannula 430 as shown in FIGS. 10H and 10I. In other embodiments, the indentations can be configured as a single circumferential groove disposed on the outside surface of cannula (not shown) to engage the ball lock mechanism at a specified length. Once the ball bearings 435, 435', 435" and 435''' are disengaged, the trocar cannula 430 may be removed from the port.

Figure 10J:
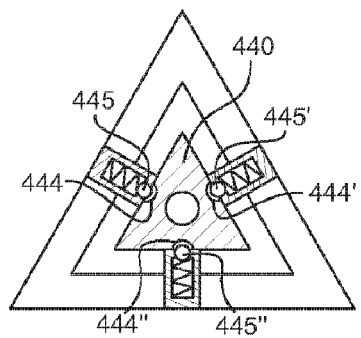
FIG. 10J is a detailed top view of a triangular cannula ball locking mechanism.
Figure 10K:
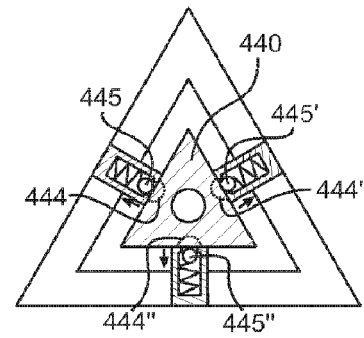
FIG. 10K is another detailed top view of a triangular cannula ball locking mechanism.

Another embodiment of a ball lock system with a trocar cannula having a triangular cross section is shown in FIGS. 10J and 10K. The ball bearings 445, 445', and 445" can interface with ball lock indentations 444, 444', and 444" on a triangular trocar cannula 440 to inhibit unintended axial movement of the trocar cannula in a locked position. Sufficient axial force applied to the trocar cannula 440 disengages the interface of the ball bearings 445, 445', and 445" from the ball lock indentations 444, 444', and 444" on the trocar cannula 440 as shown in FIGS. 10J and 10K. In other embodiments, the indentations can be configured as a single circumferential groove disposed on the outside surface of cannula (not shown) to engage the ball lock mechanism at a specified length. Once the ball bearings 445, 445', and 445" are disengaged, the trocar cannula 440 may be removed from the port.

Another embodiment of a locking system includes a pin structure on a trocar cannula that engages with a mated lock structure embedded in the access port. The locking pin engages the lock structure through the wall of the trocar cannula and remains engaged until a specialized stylet is inserted into the trocar cannula to disengage the pin.

Another embodiment of a locking system includes a magnet embedded in an insertion guide. Once the obturator is removed and the trocar cannula is in place within a patient's blood vessel, the magnet provides increased resistance to accidental removal of the trocar cannula via a magnetic force exerted upon the trocar cannula.

In embodiments of the invention having two single channel vascular access ports, different lengths of trocar cannulas for each port may be necessitated by several factors. These factors include differences in blood vessel depth at each port location, differences in patient physiology at each port location, differences in patient anatomy at each port location, and session-to-session variations in port depth. Accordingly, simultaneous use of trocar cannulas having different lengths may be required for operation of the vascular access ports. One skilled in the art will recognize that such a scenario is prone to operator error. For example, an operator may be required to consult a patient chart to select the appropriate length trocar cannulas, and then make sure to use the correct trocar cannula in each port. Furthermore session-to-session variations in patient skin thickness, limb placement, and fluid load may necessitate trocar cannulas of different lengths from session-to-session.

Additional considerations in embodiments of the invention having two single channel vascular access ports include differences in blood vessel geometry at each port location. Specifically, the ports may be implanted on blood vessels having different shapes and diameters. Accordingly, access ports of the present invention may be shaped to accommodate the differences in blood vessel geometries. During the implantation of the ports, the operating physician may select suitably shaped access ports to adapt to the geometry of the target blood vessel. Alternatively, the operating physician may determine that the target blood vessels do not necessitate ports having different shapes, and may use the same shape port in each port location.

Figure 12A:
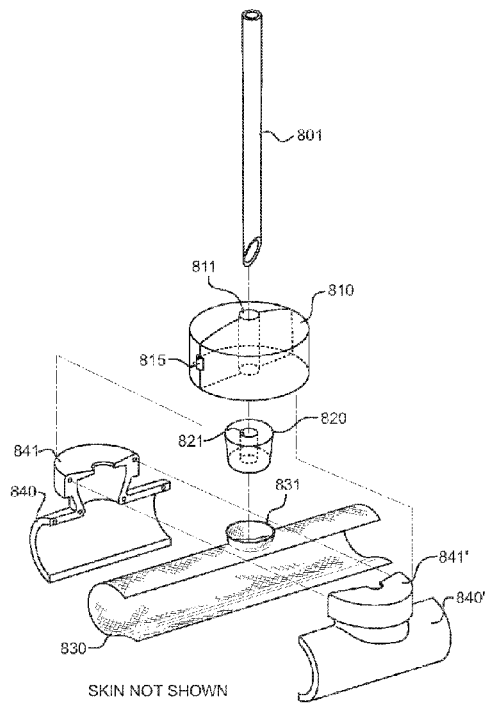
FIG. 12A is an exploded view of a circular matched guide and collar of a vascular access port.
Figure 12B:
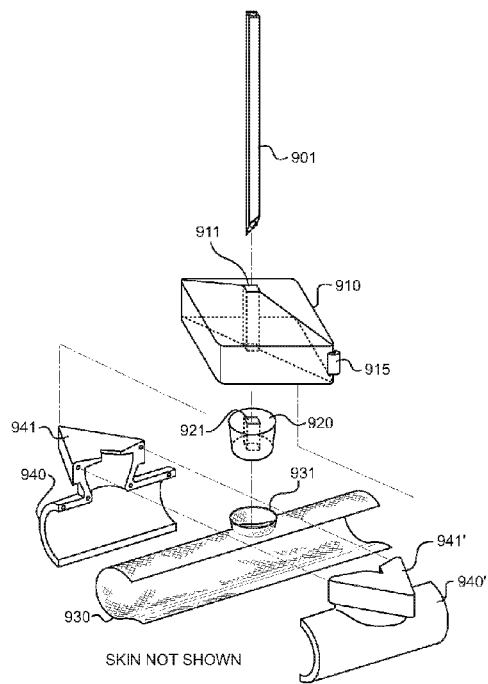
FIG. 12B is an exploded view of a rectilinear matched guide and collar of a vascular access port.
Figure 12C:
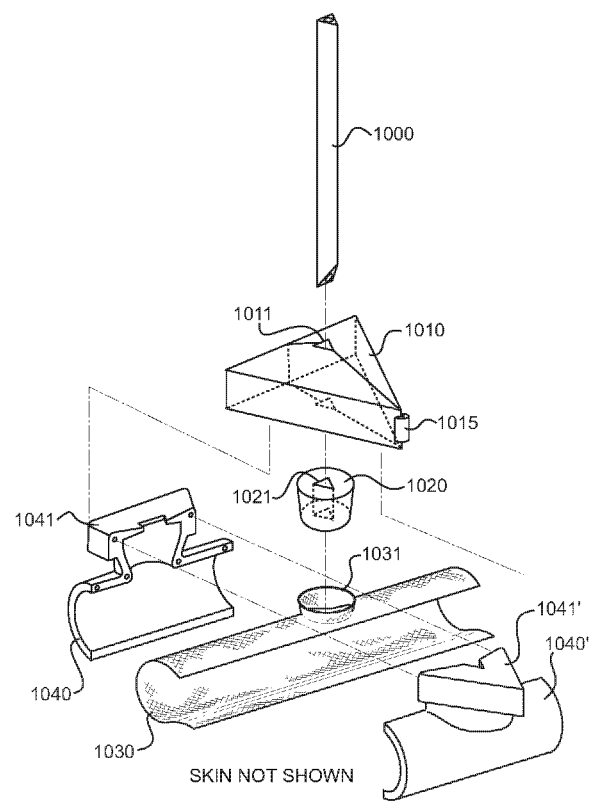
FIG. 12C is an exploded view of a triangular matched guide and collar of a vascular access port.

To accommodate the variations encountered with an embodiment having two single channel ports, and to further limit operator error, the collar, trocar cannula, and guide of an implantable vascular access port may be matched as shown in FIGS. 12A-12C. FIG. 12A generally shows a matched port set embodiment having a circular collar 841 and 841', a circular trocar cannula 801, and a circular guide 810 having a circular guide hole 811. FIG. 12B generally shows a matched port set embodiment having a rectilinear collar 941 and 941', a rectilinear trocar cannula 901, and a rectilinear guide 910 having a rectilinear guide hole 911. FIG. 12C generally shows a matched port set embodiment having a triangular collar 1041 and 1041', a triangular trocar cannula 1000, and a triangular guide 1010 having a triangular guide hole 1011.

Figure 11A:
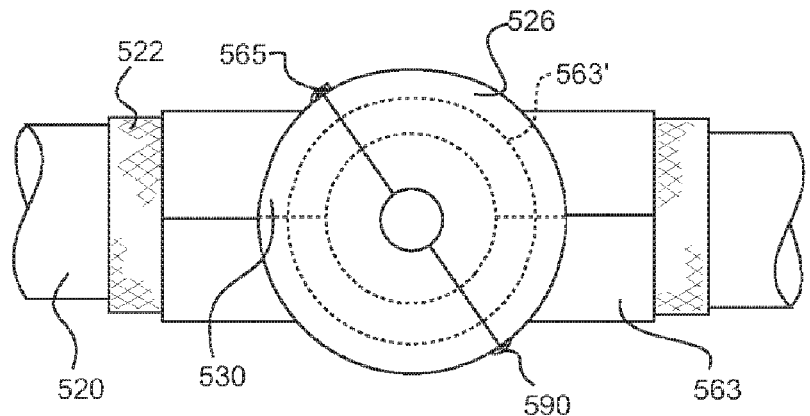
FIG. 11A is a top view of a circular alignment guide mounted on a vascular access port.
Figure 11B:
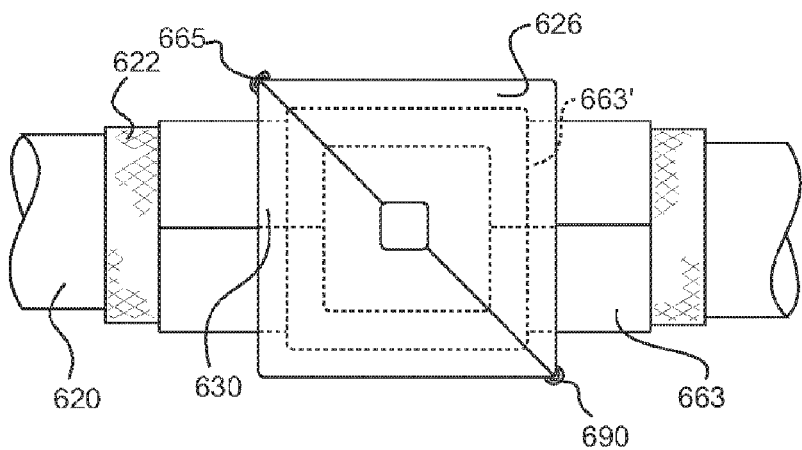
FIG. 11B is a top view of a rectilinear alignment guide mounted on a vascular access port.
Figure 11C:
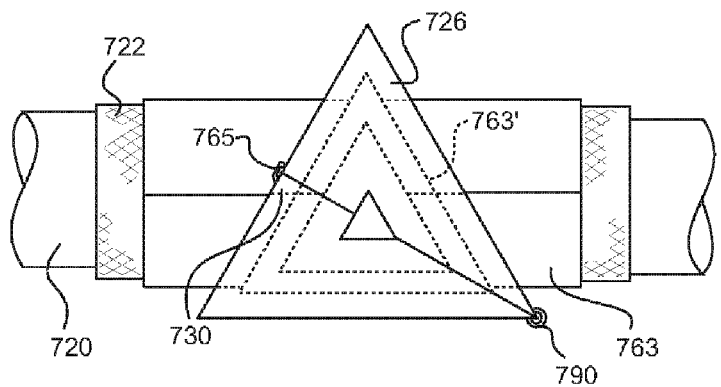
FIG. 11C is a top view of a triangular alignment guide mounted on a vascular access port.

Referring to FIGS. 11A-11C, guides having specific geometries are shown aligned with a matching port frame collar. FIG. 11A shows an embodiment of a circular guide 526 for a circular trocar cannula fitted over a portion of a patient's skin residing above an access port, and mated with a circular port frame collar 563' to ensure proper alignment over the port plug. FIG. 11B shows an embodiment of a rectilinear guide 626 for a rectilinear trocar cannula fitted over a portion of a patient's skin residing above an access port, and mated with a rectilinear port frame collar 663'. FIG. 11C shows an embodiment of a triangular guide 726 for a triangular trocar cannula fitted over a portion of a patient's skin residing above an access port, and mated with a triangular port frame collar 763'.

Matched port sets according to the invention may also include a trocar cannula locking system. Furthermore, matched port set embodiments having additional shapes are also contemplated. The components of each matched port set are not interchangeable and thus ensure that a trocar cannula of a particular shape can only be inserted into a matching port. One skilled in the art will recognize that selective use of one matched port set in one port location and a different matched port set in another location will inhibit operator error by restricting port entry to a matched trocar cannula. One skilled in the art will further recognize that during implantation, an operating physician may select from a variety of port shapes to accommodate blood vessel geometry and ensure that only the proper trocar cannula may be used therewith.

Vascular access ports of the present invention are useful for conducting hemodialysis. In general, blood from a patient is received by a dialysis device, dialyzed, and returned to the patient. In embodiments having one single channel port, a dual-lumen catheter or needle may be used to obtain two separate blood channels from one blood vessel access site. In embodiments having two single channel ports, one port may be located on a blood vessel distal to a patient's heart, while the other port is located on the same type of blood vessel proximal to a patient's heart in order to obtain blood with a high pressure differential. One skilled in the art will recognize that the pressure differential enabled by such a configuration facilitates hemodialysis by enabling the intake of unpurified blood into a dialysis device from an upstream source, and the outlet of purified blood from the dialysis device into a downstream source thereby reducing the need for the assistance of a pump.

In a dual port embodiment having two straight channels, one straight trocar cannula is inserted at an angle conducive to receiving blood from the accessed blood vessel, and a second straight trocar cannula is inserted at an angle conducive to discharging dialyzed blood back into the accessed blood vessel. The opposing angles of the inlet and outlet channel limit the mixing of treated and untreated blood flowing in and out of the cannula tips. Referring to FIGS. 2A, 3, and 4, dialyzed blood flows into a blood vessel from an angled tip 36 of a first straight trocar cannula 30, and blood flows from a blood vessel into an angled tip 35 of a second straight trocar cannula 31. The angled tip 36 of the first trocar cannula 30 is configured at an angle to discharge dialyzed blood into the accessed blood vessel. To further facilitate the flow of dialyzed blood from the trocar cannula 30 into the accessed blood vessel, the trocar cannula is inserted at an angle 40 that is sufficient to facilitate blood flow from the trocar cannula into the blood vessel. Similarly, the angled tip 35 of the second trocar cannula 31 is configured at an angle to receive blood from the accessed blood vessel. To further facilitate the flow of blood from the accessed blood vessel into the trocar cannula 31, the trocar cannula is inserted at an angle 41 that is sufficient to facilitate blood flow from the blood vessel into the trocar cannula.

During hemodialysis, a dialysis device is connected to ports on the trocar cannulas to receive blood from the accessed blood vessel and discharge dialyzed blood back to the accessed blood vessel. FIGS. 2A, 3, and 4 show cannula ports 33 and 33'. The dialysis device and cannula ports 33 and 33' may be connected by tubing constructed of a biocompatible polymer such as silicone, polyurethane, or PET.

Referring to FIG. 5, dialyzed blood flows from a blood vessel into an angled tip 55 of a first curved trocar cannula 50, and blood flows into a blood vessel from an angled tip 56 of a second curved trocar cannula 51. The angled tip 56 of the second trocar cannula 51 is configured at an angle to discharge dialyzed blood into the accessed blood vessel. To further facilitate the flow of dialyzed blood from the trocar cannula 51 into the accessed blood vessel, the trocar cannula is inserted at an angle 43 that is sufficient to facilitate blood flow from the trocar cannula into the blood vessel. Similarly, the angled tip 55 of the first trocar cannula 50 is configured at an angle to receive blood from the accessed blood vessel. To further facilitate the flow of blood from the accessed blood vessel into the trocar cannula 50, the trocar cannula is inserted at an angle 42 that is sufficient to facilitate blood flow from the blood vessel into the trocar cannula.

Similarly, vascular access ports of the present invention are also useful for ultrafiltering a patient's blood. In general, ultrafiltration is performed by substituting an ultrafiltration device for the dialysis device in the above-described blood circuit. Ultrafiltration in a dual port embodiment is performed by connecting an ultrafiltration device to the cannula ports to receive blood from the accessed blood vessel and discharge ultrafiltered blood back to the accessed blood vessel.

Vascular access ports of the present invention are also useful for other therapies requiring repeated vascular access. Such therapies include chemo-therapy treatment or any other treatment requiring repetitive intravenous drug delivery within a patient. For example, drugs may be delivered directly into the patient's blood vessel via the vascular access port.

It will be apparent to one skilled in the art that various combinations and/or modifications and variations can be made in the implantable vascular access system depending upon the specific needs for operation. Moreover, features illustrated or described as being part of one embodiment may be used on another embodiment to yield a still further embodiment.

We claim:

1. A vascular access port, comprising:
   a plug casing having a distal end to contact a vessel and a proximal end to contact subcutaneous tissue and one or more plugs disposed therein;
   the plug casing affixed to a port frame wherein the port frame is concentric to the vessel wherein the port frame is adapted to retain the plug casing and prevent compression of the vessel; and
   a releasable locking system located in the proximal end of the plug casing wherein the locking system can prevent accidental removal of a cannula upon insertion into the one or more plugs.

2. The vascular access port of claim 1, wherein the locking system can release a cannula by rotation.

3. The vascular access port of claim 1, wherein the locking system comprises one or more features of: 1) locking blades rotatable along a vertical and horizontal axis wherein upon insertion of a cannula the locking blades rotate along the vertical axis and lock upon contact with an indentation in the cannula and release in a horizontal axis upon twisting the cannula; 2) a pin that engages a wall of a trocar cannula upon removal of a stylet from the trocar cannula, and disengages from the wall of the trocar cannula upon insertion of the stylet into the trocar cannula; 3) a magnet disposed in the plug casing; and 4) a spring loaded ball to engage a groove or indentation in the cannula, wherein the groove is circumferentially disposed on the cannula.

4. The vascular access port of claim 1, further comprising a cannula having a groove or indentation keyed to a specified length and a specified port frame shape.

5. The vascular access port of claim 1, wherein the one or more plugs are composed of a self-sealing layer and layers of one or more materials that are capable of releasing agents into the vessel or other tissue contacted by the port.

6. The vascular access port of claim 5, wherein the one or more plugs have an antibiotic releasing layer in the most proximal layer that contacts subcutaneous tissue, a self sealing layer adjacent to the antibiotic releasing layer and an anti-thrombogenic agent releasing layer in the distal end.

7. The vascular access port of claim 5, wherein the agent-releasing layers in the one or more plugs are stacked in a planar configuration in the plug casing or the one or more plugs are arranged in a concentric configuration in the plug casing.

8. The vascular access port of claim 5, wherein the one or more plugs have a top sealing layer having a larger diameter than underlying layers.

9. A vascular access port of claim 1, further comprising a mesh sleeve to encase the vessel, said mesh sleeve being affixed to the plug casing.

10. The vascular access port of claim 9, further comprising a skirt that flares from the proximal end of the plug casing and contacts the vessel, wherein the skirt is disposed underneath the mesh sleeve and the mesh sleeve is composed of a flexible, woven biocompatible material.

11. The vascular access port of claim 9, wherein the mesh sleeve is fibrogenic.

12. A vascular access port comprising:
    a plug casing having a first end contacting a vessel and a second end extending in a perpendicular direction away from the vessel;
    one or more plugs located inside the port casing for insertion of a cannula to permit fluid communication from the vessel through said plugs;
    a mesh sleeve to encase the vessel having a mounting ring to secure the mesh sleeve to the plug casing;
    a retaining ring that locks onto the exterior of the mounting ring; and
    a hinged port frame having opposing cuffs that may be joined together and are shaped to encapsulate the plug casing, mounting ring, retaining ring, and at least a portion of the mesh sleeve.

13. The vascular access port of claim 12, wherein one end of the cuffs have at least one latch for securely assembling the hinged port frame.

14. The vascular access port of claim 12, further comprising
    a skirt that flares from the proximal end of the plug casing and contacts the vessel longitudinally, and
    a slit located in the mounting ring that enables the mesh sleeve to be wrapped around the skirt and the mounting ring around the plug casing.

* * * * *